United States Patent [19]
Caspers

[11] Patent Number: 5,376,132
[45] Date of Patent: Dec. 27, 1994

[54] PROSTHETIC LINER AND METHOD OF MAKING THE LINER WITH A PROSTHESIS SOCKET

[76] Inventor: Carl A. Caspers, 19251 County Rd. 156, Avon, Minn. 56310

[21] Appl. No.: 143,356

[22] Filed: Oct. 26, 1993

Related U.S. Application Data

[60] Division of Ser. No. 959,523, Oct. 13, 1992, Pat. No. 5,258,037, which is a continuation of Ser. No. 552,445, Jul. 13, 1990, abandoned.

[51] Int. Cl.$^5$ .............................................. A61F 2/80
[52] U.S. Cl. ..................................... 623/36; 623/33; 623/901; 264/222; 264/DIG. 30
[58] Field of Search ................................. 623/33–37, 623/901; 264/222, DIG. 30

[56] References Cited
U.S. PATENT DOCUMENTS

| | | | |
|---|---|---|---|
| 2,606,325 | 8/1952 | Nielson et al. | |
| 2,671,225 | 3/1954 | Schoene et al. | |
| 3,253,600 | 5/1966 | Scholl | |
| 3,322,873 | 5/1967 | Hitchcock | 264/222 |
| 3,377,416 | 4/1968 | Kandel | 264/222 |
| 3,732,578 | 5/1973 | Pollack | |
| 3,751,733 | 8/1973 | Fletcher et al. | |
| 3,858,379 | 1/1975 | Graves et al. | 53/25 |
| 3,895,405 | 7/1975 | Edwards | 12/146 M |
| 3,975,350 | 8/1976 | Hudgin et al. | 260/30.4 N |
| 3,991,424 | 11/1976 | Prahl | |
| 4,314,398 | 2/1982 | Petterssen | 623/33 X |
| 4,466,936 | 8/1984 | Schapel | 264/225 |
| 4,623,354 | 11/1986 | Childress et al. | 623/25 |
| 4,635,626 | 1/1987 | Lerman | 128/165 |
| 4,704,129 | 11/1987 | Massey | 623/25 |
| 4,828,325 | 5/1989 | Brooks | 297/458 |
| 5,007,937 | 4/1991 | Fishman et al. | 623/34 |

Primary Examiner—Randall L. Green
Assistant Examiner—D. Willse
Attorney, Agent, or Firm—Palmatier, Sjoquist & Helget

[57] ABSTRACT

A visco-elastic polymer liner for use in donning over a residual limb and fitting within the socket of an artificial limb. The liner is shaped to have its cavity formed with a volume and shape less than a volume and shape of the residual limb for both tension and tissue configuration relief while the liner has an outer surface formed with a volume and shape greater than the volume and shape of the artificial limb socket for relief of certain tissue configurations and to create weight bearing, relief and compression areas on and in the liner to absorb and dissipate shock, shear and mechanical forces through the liner otherwise transmitted to the residual limb. The liner may have imbedded on its inner cavity side electrodes adjacent muscles that are sensitive to the muscle action potentials to generate signals to a power source to move an articulable artificial limb. The liner may take the shape of a tube to be donned over a paralyzed limb similarly having electrodes imbedded in its inner cavity side adjacent neuromuscular junctions which are connected to a muscle action potential generator to activate flexion and extension of the paralyzed limb. A method for making the liner is also disclosed which comprises the making of a positive model of the residual limb, reducing the model, forming the liner about the reduced model and laminating a hard socket over a reduced model of the liner.

1 Claim, 5 Drawing Sheets

PROSTHETIC LINER AND METHOD OF MAKING THE LINER WITH A PROSTHESIS SOCKET

This is a division of U.S. patent application Ser. No. 07/959,523, filed Oct. 13, 1992, now U.S. Pat. No. 5,258,037, which is a file wrapper continuation of U.S. patent application Ser. No. 07/552,445, filed Jul. 13, 1990, now abandoned.

BACKGROUND OF THE INVENTION

The present invention relates to prosthetic devices and more particularly to an improved liner for prosthetic devices including artificial limbs that also may be articulable or bionic.

An amputee is a person who has lost part of an extremity or limb such a leg or arm which commonly may be termed as a residual limb. Residual limbs come in various sizes and shapes with respect to the stump. That is, most new amputations are either slightly bulbous or cylindrical in shape while older amputations that may have had a lot of atrophy are generally more conical in shape. Residual limbs may further be characterized by their various individual problems or configurations including the volume and shape of a stump and possible scar, skin graft, bony prominence, uneven limb volume, neuroma, pain, edema or soft tissue configurations.

Figure 1:
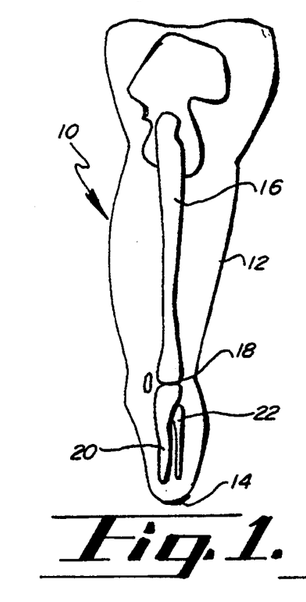
FIG. 1 is a side elevational view of the tissue and skeletal structure of an amputee's residual limb.
Figures 2, 4:
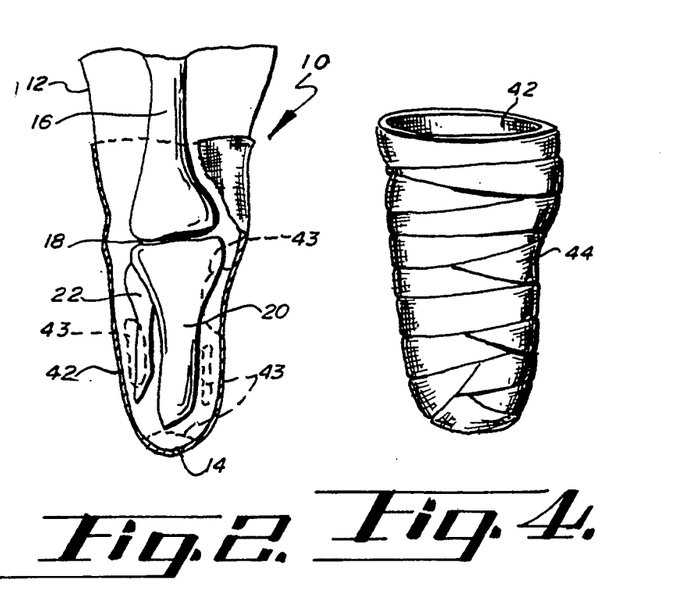
FIG. 2 is a front elevational view of a residual limb with a volume and shape and the skeletal structure visible while donning a light cotton marking sock.
FIG. 4 is a front elevational view of a plaster wrap or cast of the residual limb of FIG. 2 constituting a negative model of the residual limb.

Referring to FIGS. 1 and 2, a below the knee residual limb 10 is shown and described as a leg 12 having been severed below the knee terminating in a stump 14. In this case, the residual limb 10 includes soft tissue as well as the femur 16, knee joint 18, and severed tibia 20 and fibula 22. Along these bone structures surrounded by soft tissue are nerve bundles and vascular routes which must be protected against external pressure to avoid neuromas, numbness and discomfort as well as other kinds of problems. A below the knee residual limb 10 has its stump 14 generally characterized as being a more bony structure while an above the knee residual limb may be characterized as including more soft tissue as well as the vascular routes and nerve bundles.

Figure 3:
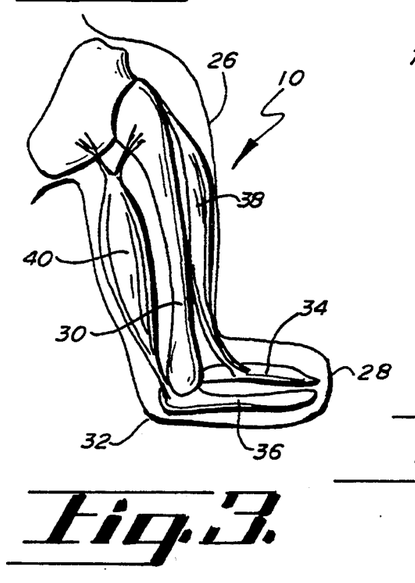
FIG. 3 is a side elevational view of a residual limb in the form of an amputated arm showing the skeletal and muscular structure of the residual limb.

Referring to FIG. 3, amputees who have lost a part of their arm 26, which terminates in a stump 28 also may be characterized as having vascular routes, nerve bundles as well as soft and bony tissues. The residual limb 10 includes the humerus bone 30 which extends from below the shoulder to the elbow from which the radius 34 and ulna 36 bones may pivotally extend to the point of severance. Along the humerus bone 30 are the biceps muscle 38 and the triceps muscle 40 which still yet may be connected to the radius 34 and the ulna 36, respectively.

In some respects, the residual limb amputee that has a severed arm 26 does not have the pressure bearing considerations for an artificial limb but rather is concerned with having an artificial limb that is articulable to offer functions typical of a full arm, such as bending at the elbow and grasping capabilities. An individual who has a paralyzed limb would also have similar considerations wherein he or she would desire the paralyzed limb to have some degree of mobility and thus functionality.

Historically, artificial limbs typically used by a leg amputee were for the most part all made out wood such an Upland Willow. The limbs were hand carved with sockets for receiving the stump 14 of the residual limb 10. Below the socket would be the shin portion with the foot below the shin. These wooden artificial limbs were covered with rawhide which often were painted. The sockets of most wood limbs were hollow as the limbs were typically supported in the artificial limb by the circumferential tissue adjacent the stump 14 rather than at the distil end of the stump 14.

Some artificial limbs in Europe were also made from forged pieces of metal that were hollow. Fiber artificial limbs were also used which were stretched around a mold afterwhich they were permitted to dry and cure. Again, these artificial limbs were hollow and pretty much supported the residual limb about the circumferential tissue adjacent the stump 14.

All of these various artificial limbs have sockets to put the amputee's stump 28 thereinto. There are generally two categories of sockets. There are hard sockets wherein the stump goes right into the socket actually touching the socket wall without any type of liner or stump sock. Another category of sockets is a socket that utilizes a liner or insert. Both categories of sockets typically were opened ended sockets were they had a hollow chamber in the bottom and no portion of the socket touched the distil end of the stump 14. So, the stump was supported about its circumferential sides as it fits against the inside wall of the sockets.

These types of sockets caused a lot of shear force on the stump 14 as well as had pressure or restriction problems on the nerve bundles and vascular flow of fluid by way of the circumferential pressure effect of the socket on the limb. This pressure effect could cause a swelling into the ends of the socket where an amputee may develop severe edema and draining nodules at the end of their stump 14.

With time, prosthetists learned that by filling in the socket's hollow chamber and encouraging a more total contact with the stump and the socket, the swelling and edema problems could be eliminated. However, the problematic tissue configurations, such as bony prominences, required special consideration such as the addition of soft or pliable materials to be put into the socket.

Today, most artificial limbs are constructed from thermoset plastics such a polyester resins, acrylic resins, polypropylenes and polyethylenes, which are perhaps laminated over a nylon stockinette which also may be impregnated by the various resins.

In the past, most artificial limbs were suspended from the amputee's body by some form of pulley, belt or strap suspension often used with various harnesses and perhaps leather lacers or lacings. Another method of suspending artificial limbs is known as the wedge suspension wherein an actual wedge is built into the socket which is more closed at its top opening. The wedge in the socket cups the medial femoral condyle or knuckle at the abductor tubical. Yet another form of suspension is referred to as the shuttle system or a mechanical hookup or linkup wherein a thin suction liner is donned over the stump that has a docking device on the distal end which mechanically links up with its cooperative part in the bottom of the socket chamber. Sleeve suspensions were also used wherein the amputee may use a latex rubber tube which forms into a rubber-like sleeve which would be rolled on over both the top of the artificial limb and onto the amputee's thigh. The sleeve suspensions have been used in combination with other forms of suspension techniques.

The first artificial limb socket liners were made with molded horsehide leather covered with strips from extruded sheets of rubber glued to the leather as the liner was built up over a positive cast of the residual limb. As before, stump socks typically made of cotton or wool were used with these first liners as well as with the earlier hard sockets.

The next major socket liner was formed from an expanded foam such as polyurethane foam as sold by Durr-Fillauer Medical, Inc. of Chatanooga, Tenn. After a positive cast was made of the residual limb, a cone-like structure of the hard foam plastic was formed and heated. Next, the expanded foam was pulled over the cast of the residual limb in an effort to form it to the limb after which the foam was cooled and its shape was retained over the positive cast. Thereafter, a hard shell socket could be built or laminated over the liner from which a shin and foot of the artificial limb could be attached.

Another type of socket liner was made from a combination of silicone and gauze being sandwiched in between two pieces of leather. However, this type of liner had problems in that it was much too rigid, wouldn't stretch and eventually loosened up and migrated thereby becoming ineffective.

The next group of socket liners were made from the impregnation of a cotton stockinette with silicone resins formed over a positive cast of the residual limb. The problem with these types of liners is that the silicone could not migrate or stretch and was often short lived in that sweat from the residual limb would break down the silicone and create pungent and unsanitary conditions.

Another type of silicone liner without the impregnated stockinette has been utilized to create suction about the residual limb for use in combination with perhaps a shuttle or mechanical link up device with the socket. However, these types of liners offered no yield or cushion and required the wearing of stump socks.

While some of these devices addressed some of the problems associated with prosthetics, none of the artificial limbs, liners and sockets, individually or in combination offered a prosthesis that presented a total contact relationship with the residual limb; absorbed and dissipated shear, shock and mechanical forces transmitted to the limb tissues by the artificial limb; controlled perspiration of the residual limb; controlled residual limb volume; and, promoted equal weight distribution while having a long life expectancy.

There is a need for a liner to be used with prosthetic devices that will offer total contact relationship with the residual limb; provide hypobaric suction suspension with a sticky or tacky surface condition; absorb and dissipate shock, mechanical and shear forces typically associated with ambulation, twisting and turning and weight bearing with an artificial limb; control perspiration; control residual limb volume by way of even weight distribution; and offer relief for the various tissue configurations that plague residual limbs while yet being of long life.

SUMMARY OF THE INVENTION

A visco-elastic polymer liner for use in donning over a residual limb and fitting within the socket of an artificial limb. The liner is shaped to have its cavity formed with a volume and shape less than a volume and shape of the residual limb for both tension and tissue configuration relief while the liner has an outer surface formed with a volume and shape greater than the volume and shape of the artificial limb socket for relief of certain tissue configurations and to create weight bearing, relief and compression areas on and in the liner to absorb and dissipate shock, shear and mechanical forces through the liner otherwise transmitted to the residual limb. The liner may have imbedded on its inner cavity side electrodes adjacent muscles that are sensitive to the muscle action potentials to generate signals to a power source to move an articulable artificial limb. The liner may take the shape of a tube to be donned over a paralyzed limb similarly having electrodes imbedded in its inner cavity side adjacent neuromuscular junctions which are connected to a muscle action potential generator to activate flexion and extension of the paralyzed limb. A method for making the liner is also claimed which comprises the making of a positive model of the residual limb, reducing the model, forming the liner about the reduced model and laminating a hard socket over a reduced model of the liner.

A principal object and advantage of the present liner is that it provides total environment control about the tissue of the residual or paralyzed limb by way of a total contact relationship between the liner and the tissue.

Another advantage and object of the present invention is that it has a tacky or sticky surface which permits the liner to actually tack up to the limb tissue and provide a hypobaric suction when used as a socket liner which eliminates a bulky suspension apparatus as well as control on the residual limb volume and perspiration.

Another object and advantage of the present invention is that the liner, when utilized with an artificial limb socket, totally absorbs and dissipates shock, shear and mechanical forces which are normally transmitted directly to the tissues of the residual limb from the artificial limb during weight bearing, ambulation, twisting and turning.

Another advantage and object of the present invention is that the total contact relationship between the residual limb tissues, the liner and the artificial limb socket permits equal weight distribution resulting in lower pounds per square inch pressure on limb tissues thereby permitted extended comfortable wear of an artificial limb heretofore not known.

Another advantage and object of the present invention is that the visco-elastic, energy-absorbing, flexible polymer liner will stretch, move or creep internally while having a memory for the liner to return to its original shape.

Another advantage and object of the present invention is that the liner when used with a socket and artificial limb may be used with any means of suspension although suction socket with a mechanical link-up appears advantageous.

Another principal object and advantage of the present liner is that the polyurethane elastomer material permits additional buildup and removal of material for adjustment of the liner over time that is easy and simple without the need of additional catalysts.

Yet another advantage and object of the present invention is that the liner is durable for long wear and is readily cleanable with soap and water to provide an odor free clean environment for a residual limb or a paralyzed limb.

A final principal object and advantage of the present invention is that an amputee with a residual limb may simply don the liner and place the limb within a socket without the need of additional padding or stump socks which has normally been the case until this invention.

BRIEF DESCRIPTION OF THE DRAWINGS

FIG. 5 is a front elevational view of a plaster positive model of the residual limb of FIG. 2 made from the mold of FIG. 4;

DESCRIPTION OF THE PREFERRED EMBODIMENT

Referring to FIGS. 1-5, normally amputees are seen by the prosthetist post operatively after they have had primary wound healing. While the residual limb 12 consists of either a leg 12 or an arm 26, the amputees are evaluated for the size and shape of their stump 14 or 28 with additional considerations given to scar, skin graft, bony prominence, uneven limb volume, neuroma, pain, edema or soft tissue configurations. Through conversations, the amputees are also evaluated as to what their activity levels are.

Next, a single ply thin cotton casting sock 42 is then placed over the residual limb 10. Certain tissue configuration locations as well as pressure sensitive areas are then marked with indelible ink 43 on the casting sock 42. Next, an orthopedic plaster wrap 44 that has been dipped in water is formed about the residual limb. After the wrap has been permitted to set and harden, the residual limb 10 is withdrawn from the plaster wrap 44 leaving the casting sock 42 adhered to the plaster wrap. Various separating or releasing media may be used on the residual limb before donning of the casting sock 42, such as a baby powder, vaseline or petroleum jelly, which assists in the removal of the residual limb from the plaster wrap which constitutes the first negative mold of the residual limb 10.

The plaster wrap 44 or first negative mold of the residual limb 10 is next filled with plaster, such as dental plaster, and a centrally located mandrel or pipe 48 is positioned within the plaster cast for later key positioning within a jig or for simply supporting the plaster cast 46 after it is removed from the plaster wrap 46. Again, known separating agents may be used between the plaster wrap 44 and the plaster cast 46.

The plaster cast 46, once removed from the plaster wrap 44, constitutes the original prototype and first positive model 46 of the residual limb 10. As can be seen in the original prototype 46 in FIG. 5, the ink marks 43 readily transfer over to the plaster cast 46 for consideration of the residual limb's volume and shape, category and tissue configurations, such as a scar, skin graft, bony prominence, uneven limb volume, neuroma, edema, pain, pressure sensitive areas and soft tissue. Certain of these areas will require the liner 90 to have varying degrees of thickness and density to accommodate these considerations.

Figures 6, 7, 8, 9:
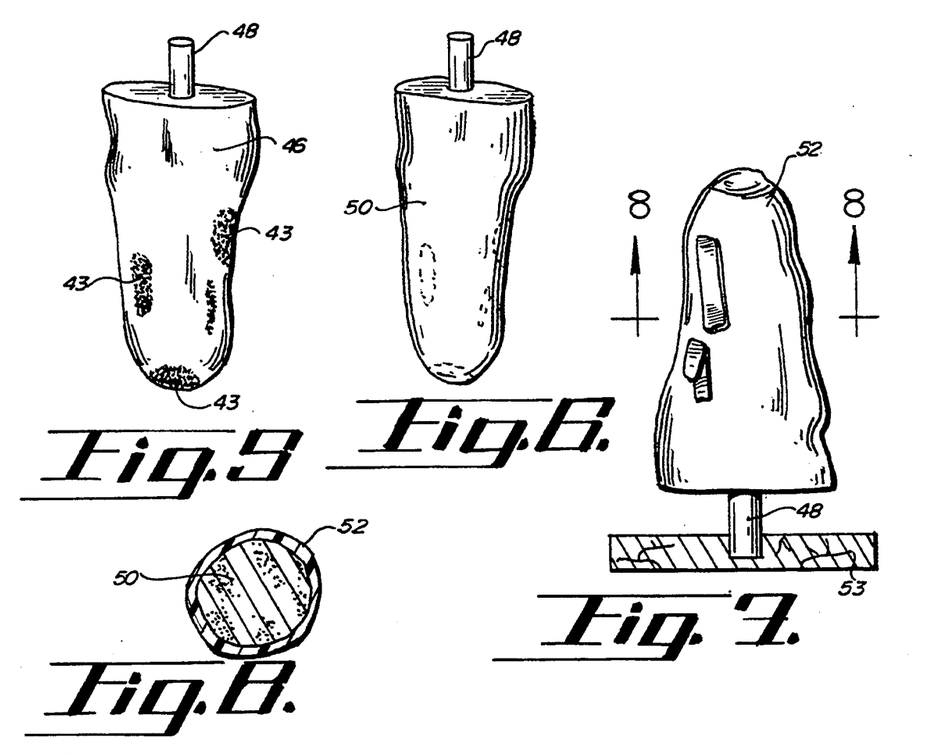
FIG. 6 is a reduced positive model of the residual limb of FIG. 2 formed by reduction of the positive model of FIG. 5 having a volume and shape less than that of the positive model.
FIG. 7 is a front elevational view of the reduced positive model or prototype of FIG. 6 mounted in a jig with a liner filler medium stretched thereover.
FIG. 8 is a cross-section take along lines 8—8 of FIG. 7.
FIG. 9 is a front elevational view of the reduced positive model of the residual limb with a second plaster wrap over the filler medium and reduced positive model of the limb as shown in FIG. 7.
Figure 9:
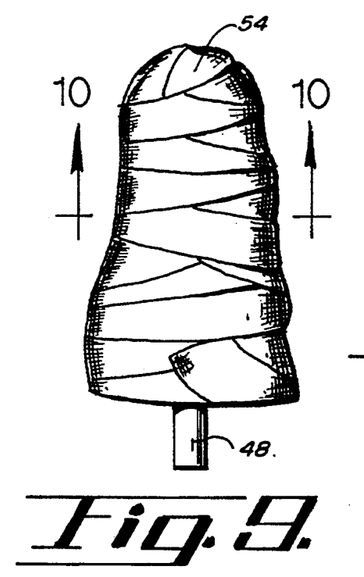

Thus, referring to FIG. 6, the original prototype 46 of FIG. 5 is reduced or built up to form the reduced positive model of the residual limb 50. The reduction of this positive model will result in a tension factor on the liner 90 when it is stretched and donned by the residual limb 10, which is a little larger than the volume and shape of the inner cavity 91 of liner 90, as will become clear.

Applicant presently contemplates that computer controlled mills will assist the prosthetists in either shaving off or melting off in a more accurate fashion portions of the original prototype 46 to create the reduced positive model 50 of the residual limb 10.

It is important that the reduced positive model not be reduced in size too much as to create a shear force upon the tissues of the residual limb 10 creating problems.

The prosthetist must next consider what thickness he or she wishes the liner 90 to have. Normally the liner 90 is between five-eights to three-quarters of an inch thick at the stump end 14 and roughly about three-sixteenths to a quarter of an inch thick around the entire residual limb. Additional considerations would include making the liner thinner where specific weight bearing areas of the residual limb would be located as well as making certain areas of the liner 90 thicker to displace and compress the liner 90 in a manner to disperse pressure away from certain tissue configurations. It is also known that where a person is more fleshy, such as in the femur 16 area in the above the knee amputation, the liner 90 would have generally thinner dimensions to add weight bearing areas to the soft tissues. Where there exists a bony prominence, such as in the below the knee amputee, the liner 90 may be a little thicker to disperse the weight bearing areas.

With these considerations in mind, the prosthetists takes the reduced positive model 50 with its mandrel 48 and mounts the model 50 in jig 53 suitably upside down for ease of working as seen in FIG. 7. Thereafter, a filler medium, such a thermoplastic foam 52, is then built on and about the reduced positive model 50 which actually represents the thickness of the liner 90 to be made. The filler medium 52 may be a wool stump sock or various types of expanded thermoplastic foams will also work well. The thermoplastic foams 52 can be readily formed into the shape of a cone and heated. Thereafter, the heated foam 52, which becomes flexible is formed over the reduced positive model 50 and perhaps vacuumed thereto by way of an evacuated plastic bag being placed over the thermoplastic foam 52. Sheets of the foam 52 that are formed into cone-like structures are available from previously mentioned Durr-Fillauer Medical, Inc. of Tennessee.

As stated, the expanded thermoplastic foam, such as a polyurethane foam or other such expanded foam products such as polyethylene or polypropylene, represents the space where the liner 90 will be. Thus, additional pieces of the foam 52 may be added to the reduced positive model 50, such as the distal end of the stump 14 to form a distal end cap as well as or other areas which may require additional thicknesses due to tissue configurations.

Figure 10:
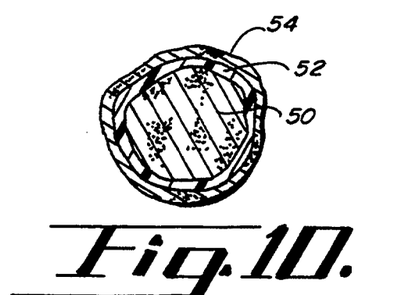
FIG. 10 is a cross sectional view taken along lines 10—10 of FIG. 9.

After a releasing or separating medium has been applied to the thermoplastic foam 52, a second plaster wrap 54 is applied over the foam 52 thereby creating a second enlarged negative mold 54 as shown in FIGS. 9 and 10. Thus, the reduced positive model 50 of the residual limb 10 is in a predetermined spaced relationship with the second plaster wrap 54 by way of the thermoplastic foam interface 52.

Figure 11:
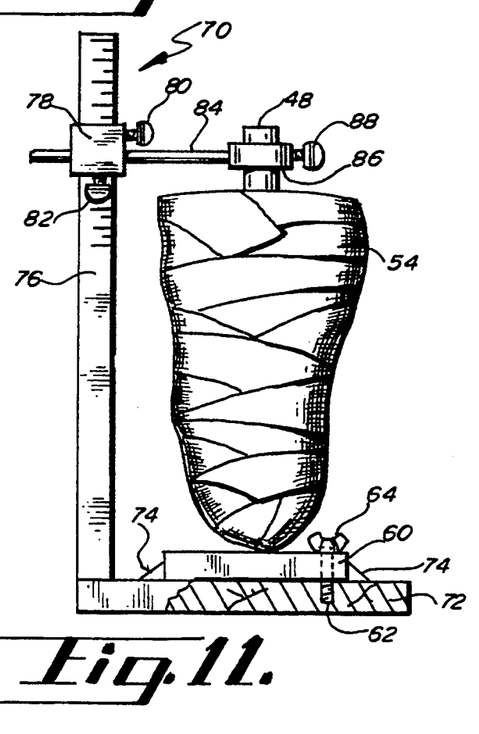
FIG. 11 is an elevational view of the jig for keying the second plaster wrap of FIG. 9 about the reduced positive model of the residual limb of FIG. 6 with the base of the jig partially broken away.

Referring to FIG. 11, the second plaster wrap 54 has an adaptor block 60, suitably made of wood or foam, affixed to its bottom such as by glue.

The block 60 appropriately has a threaded aperture 62 through which a wing nut screw 64 rotatably may pass. The plaster wrap 54 with its adapter block 60 is now ready for placement within the transfer jig 70. Transfer jig 70, as shown in FIG. 11, is a memory device for repeatedly keying the reduced positive model 50 and the second plaster wrap 54 should additional liners 90 be required to be built over time. Transfer jig 70 includes a horizontal plate 72 with keying connectors or ridges 74 which will permit indexing the adaptor block 60 therein for repeated and exact placement of the second plaster wrap 54 upon the transfer jig 70.

Transfer jig 70 also includes a calibrated vertical support 76 having a first collar 78 which adjusts vertically and horizontally and may be secured with respect to those two planes by collar fastener 80. First collar 78 and second collar fastener 82 support, hold and key a horizontal extension 84 which has a second horizontal collar 86 located at its opposing end. The second collar 86 similarly has a collar fastener 88 for locking the collar 86 about mandrel 48.

By this arrangement, reduced positive model 50 of residual limb 10 and the second plaster wrap 54, which is the negative mold of the socket may be keyed together repeatedly in the exact relationship so that the liner 90 may be repeatedly poured and shaped into the same shape.

With the thermoplastic foam 52 removed from between the reduced positive model 50 and the second plaster wrap 54, the liner 90 in its liquid and moldable form may be introduced into the enlarged negative mold 54. However, the liquid may first be subjected to vacuum, such as in a desiccator, to draw out excess gases and bubbles. Urethane liner 90 is suitably made from a visco-elastic polymer which is energy absorbing and flexible exhibiting a flowability or internal movement character with recovery of shape or memory. Applicant has found that a polyurethane elastomer is suitably appropriate in that it is further washable, durable, bacterialstatic and fungistatic. Urethanes are technically called a carbamate ester which is made from a combination of isocyanates and alcohols. More definitively, applicant has found that an aromatic diisocyanate and elastisizing polyols, such as diols or triols, form suitably urethanes or polyurethanes.

Applicant has found that a preferable polyurethane includes the combination of an antioxydant with free toluene diisocyanate and a blend of polyether polyols with bismuth carboxylate. These components are commercially available from Rieckens Orthodics Laboratories of 401 North Green River Road, Evansville, In. 47715 and has been used in the past as sole material or inlay for use with shoes. Although energy absorbing polymers have been used as sole or inlays for shoes, they have never been utilized in the context of the present invention or prosthetic.

Applicant has also found that vinyl resins or moldable thermoplastics exhibiting visco-elastic polymer qualities, energy absorption, flexibility, flowability and recovery also will work in forming liner 90.

Once the diiosocyanate and polyols components have been mixed together forming viscous fluid with the appropriate and predetermined durometer, the fluid is poured into the second plaster wrap 54. The reduced positive model 50 of the residual limb 10 is then placed into the second plaster wrap 54 and keyed into the transfer jib 70 as if thermoplastic foam 52 was still interfaced between the model 50 and the wrap 54. A releasing agent, such as a silicone base mold separator, may be utilized between the wrap 54 and the model 50 so that the liner 90 will readily separate after be permitted to set and cure after one or two hours. Separators are also available from Riechens Orthodic Laboratories.

Referring to FIGS. 12–16, the prosthetist next has the amputee don the urethane liner 90 over his or her residual limb 10 after the urethane liner 90 has been cleaned up and washed with soap. If the polyurethane liner 90 is of extensive length, the amputee may need a wetting agent such as a petroleum jelly which will readily dissipate. Otherwise, the liner 90 is slid or rolled onto the amputee's residual limb 10. Should the liner 90 require some build up, the freshly mixed components will readily adhere to the liner 90.

Figure 12:
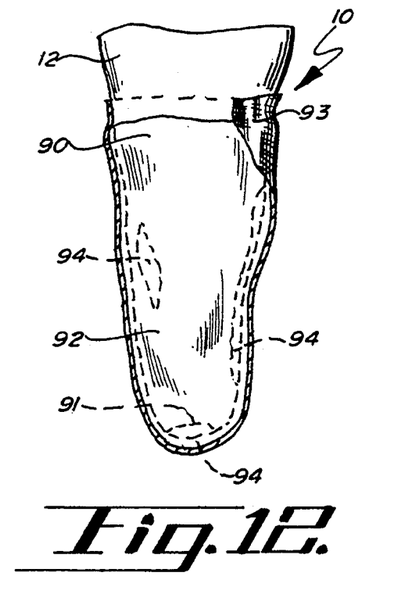
FIG. 12 is a front elevational view of the residual limb donning the liner of the present invention with a light cotton marking sock thereover.

Thereafter, another single ply thin cotton casting sock 93 is then placed over the liner 90 which is marked with the indelible ink 94 for a second consideration of certain previously mentioned tissue configurations such as bony prominences, pressure areas and scar problems. This step is necessary because once the liner 90 is donned over the residual limb 10 with some degree of tension, some of the relief, shape and volume adjustments previously made become dissipated.

Figure 13:
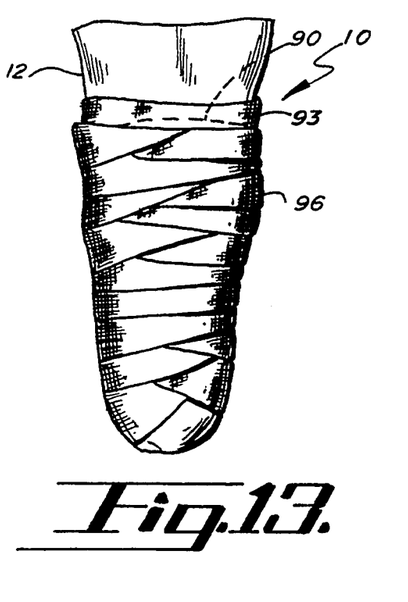
FIG. 13 is a front elevational view of the residual limb with liner and cotton sock of FIG. 12 having a third plaster wrap thereover which is a negative model of the socket.

Thereafter, a third plaster wrap 96 or a negative model of the artificial limb socket 104 is then made about the residual limb 10 with the liner 90 and marked up casting sock 93 thereon.

Figures 14, 15, 16:
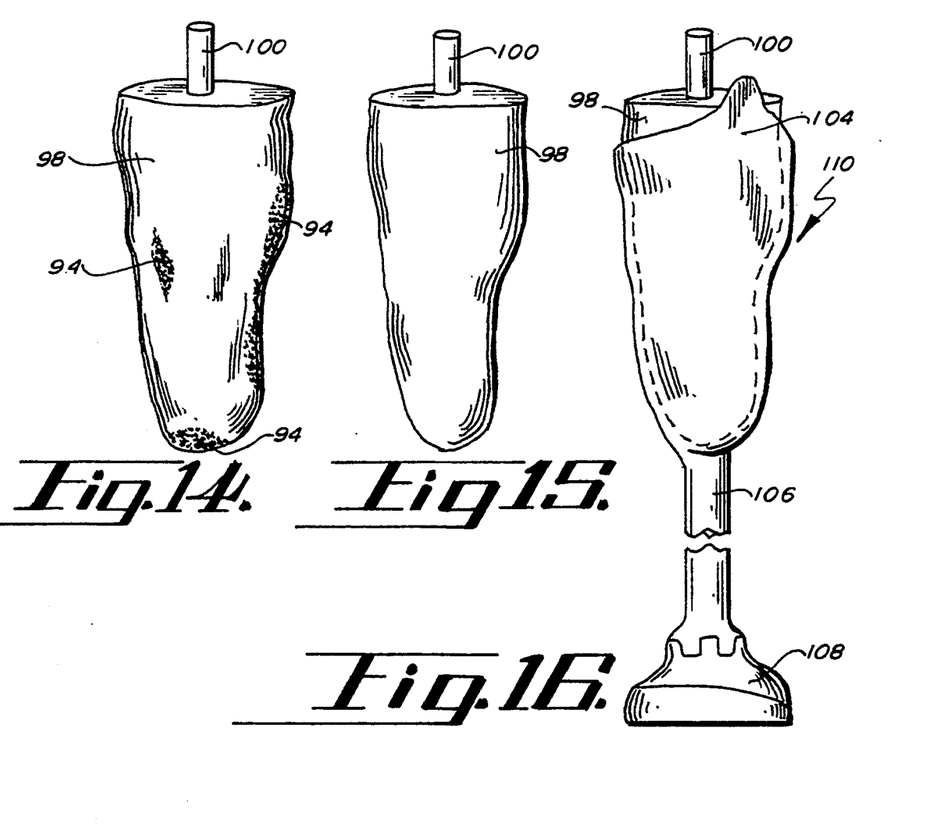
FIG. 14 is a plaster cast or positive model of the socket made from the plaster wrap of FIG. 13.
FIG. 15 is a reduced positive model of the socket made from the model of FIG. 14 having a volume and shape less than that of the positive model of FIG. 14.
FIG. 16 is a side elevational view of the socket and remaining parts of an artificial limb laminated or built about the reduced positive model socket of FIG. 15.

After the third plaster wrap 96 has cured and the residual limb 10, liner 90 have been removed from the third plaster wrap 96 or negative model of the socket, a plaster cast or positive model of the socket 98 is made from dental plaster. Suitably a mandrel 100 is placed in the plaster 98 to assist in construction of the socket 104. As seen in FIG. 14, a positive model of the socket 98 has the ink marks 94 for certain reduction and build up considerations for various tissue configurations and so on.

Next, the positive model of the socket 98 is milled or shaved to create a reduced positive model of the socket 102 which is necessary to create weight bearing areas and compression upon the liner against the inner cavity 91 of the liner 90 on the residual limb and upon the outer surface 92 of the liner 90 upon the socket 104.

Figures 17, 18:
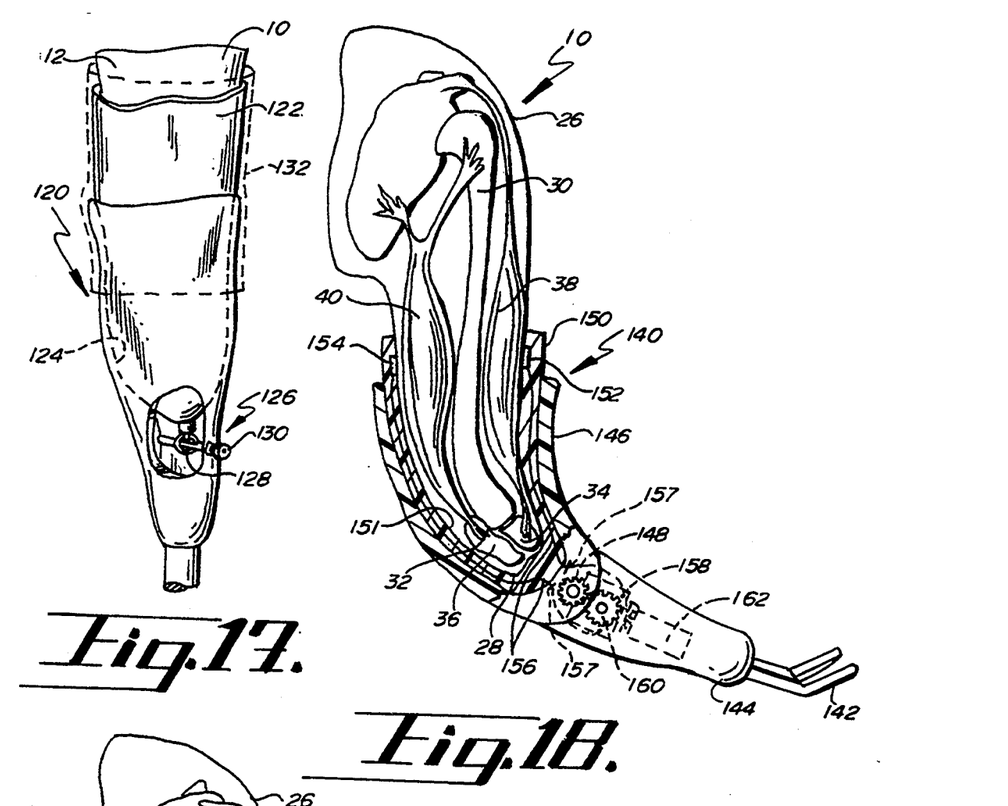
FIG. 17 is an elevational view of a mechanical link-up, hook-up or interlocking linkage for securing the residual limb liner to an artificial limb.
FIG. 18 is a side elevational view of an amputee's residual limb donning a bionic or articulable limb partially broken away in an extension position.

Referring specifically to FIG. 16, the artificial limb 110 includes its socket 104, shin 106 and foot 108. The limb 110 may be constructed by way of polyester or acrylic resins laminated over nylon stockinettes or by way of thermoset plastics including polypropylene and polyethylene. The artificial limb 110 may use various suspension techniques as mentioned. Once the socket 104 has been formed by lamination over the reduced positive model of the socket 102, the artificial limb 110 is most suitable for total contact hypoboric suction shuttle suspension as shown in FIG. 17. By this arrangement, the liner 122 is donned by the artificial limb and placed within socket 124. A releasably mechanical interlocking hookup or linkage 126 includes a ring 128 supported by a mounting means in the liner and a pin 130 mounted in the socket adjacent the shin. As previously stated, a sleeve 132 may also be placed over the artificial limb 120 and the leg 10.

The visco-elastic, energy absorbing, flexible polymer liner of the present invention has applications beyond that of merely being a total contact hypoboric suction, equal weight distribution socket liner. That is, the polyurethane liner, which readily tacks up to the skin of the human body to the point of almost actually becoming part of the skin readily permits the proper location of electrodes for use and application of bionic artificial limbs or the application of creating movement of paralyzed limbs.

Figure 19:
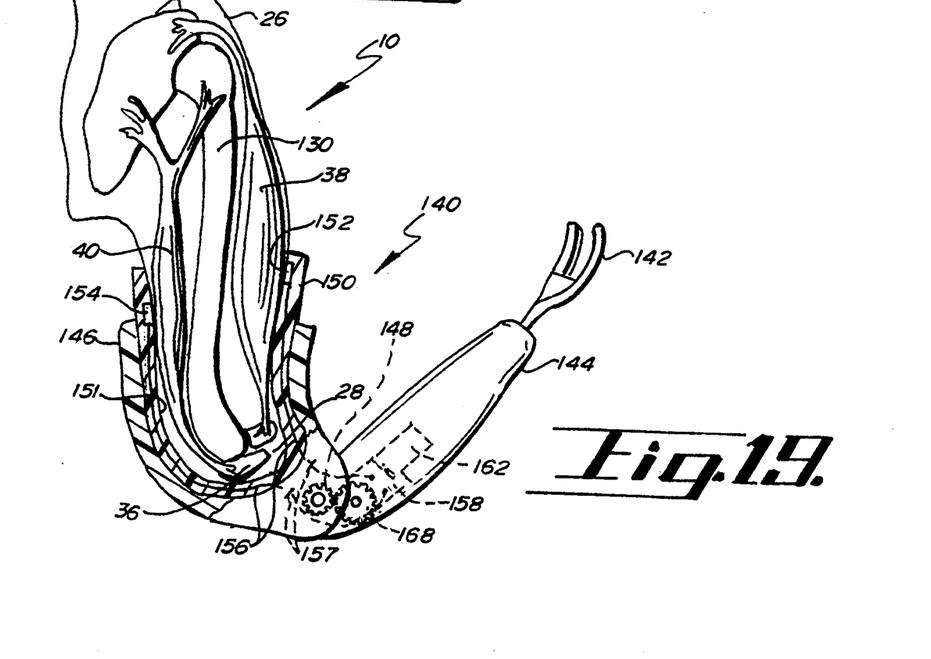
FIG. 19 is the residual limb and artificial limb of the FIG. 18 in its flexion position.

Referring to FIGS. 18 and 19, the application of the present invention in a bionic artificial limb or arm 140 will be explained. The amputee's arm 26 consists of a stump 28 below the elbow 32 wherein the radius 34 and ulna 36 bones have been severed. The amputee has normal and innervated bicep and tricep muscles 38 and 40 along the humerus with the exception that their lower most connection to the radius and ulna, which have been severed, provide no lever for these muscles to permit a function.

Consequently, a bionic or articulable artificial arm 140, as is known, typically would have a moveable hook or hand 142 and a pivotally mounted motor driven forearm 144 connected to the above elbow socket section 146. The socket section 146 has a pivot gear 148. The polyurethane liner 150 of the present invention includes an inner cavity 151 which has a biceps electrode 152 and a triceps electrode 154. The electrodes 152 and 154 touch the skin and lie over the muscles 38 and 40 in a predetermined location to monitor muscle action potential. The electrodes 152 and 154 are then wired 156 through the liner 150 to touch plates 157 which are further wired into the bionic arm 140. Signals from the electrodes 152 and 154, which sense muscle action potentials, are amplified and relayed to a forearm 144 control motor 158 which operates gear 160, all of which are powered by battery 162.

In operation, the amputee consciously flexes his biceps muscle 38. The muscle action potential is then sensed by bicep electrode 152 after which it is relayed and amplified to engage motor 158 and gear 160 to drive the forearm portion 144 of bionic arm to a flexion motion. When the amputee wishes to have the forearm 144 move into an extension or downward motion, the amputee simply flexes his or her tricep muscles 40. The muscle action potential is then sensed by triceps electrode 154 which similarly engages motor 158 and gear 160 in reverse operation to move the forearm 144 downwardly.

The liner 150 of the present invention permits this operation with repeated accuracy due to the liners construction, location of the electrodes 152 and 154 and wires 157 within the liner by way of forming the liner as previously stated. The exact construction and donning of the liner 150 will assure that electrodes 152 and 154 are repeatedly placed over the proper location on the amputee's skin and wires 156 will engage or touch plates 157.

Figure 20:
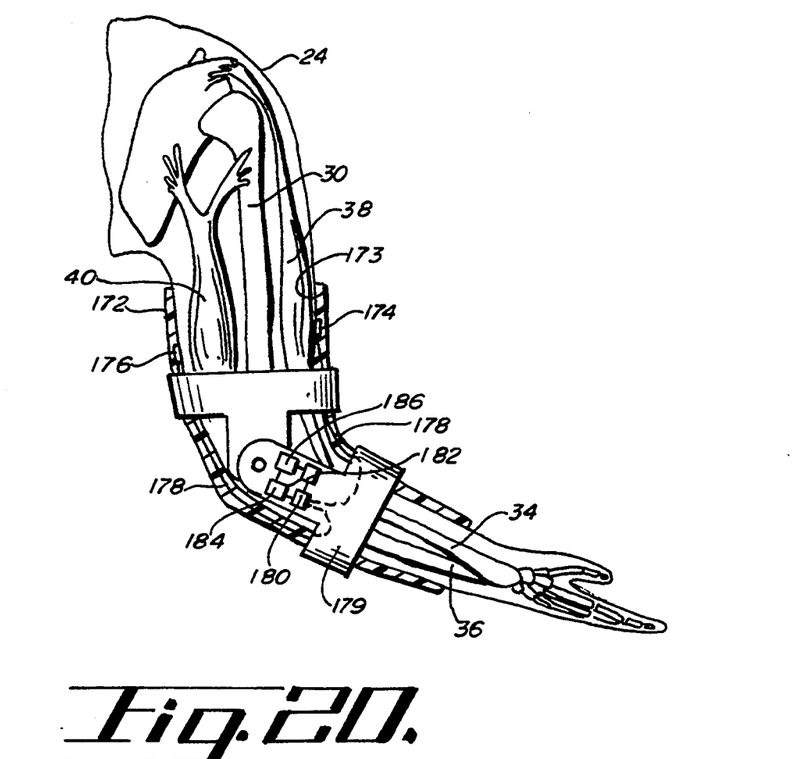
FIG. 20 is an elevational view of a paralyzed upper limb or arm donning a bionic harness for actuating paralyzed muscle movement.

Referring to FIG. 20, the liner of the present invention has application for individuals who have a paralyzed limb 170 wherein the paralysis is due to a disconnection along the nerve pathways between the brain and the muscle. In other words, the muscles 38 and 40, once properly stimulated, will permit flexion and extension of the paralyzed individuals's forearm.

Initially the proper locations to stimulate the bicep and tricep muscles 38 and 40 must be predetermined by known means, such as a "Tens device." Thereafter, a polyurethane liner or tube 172 is formed as previously disclosed herein having an inner wall 73. The bicep and tricep electrodes and 174 and 176 are then placed within the liner during its formation with connection wires 178. Wires 178 are connected to a bionic harness 179 as shown. The electrodes 174 and 176 are connected by way of the wires 178 to a muscle action potential generator 180 which receives signals from amplifier 184 and limb flexion or extension signal receiver 186, all of which are powered by battery 182. When a flexion or extension signal is received by the receiver 186, a muscle action potential is discharged at the electrodes 174 or 176 likely located near a neuromuscular junction which will initiate either flexion or extension.

Again, it is the unique method of construction and materials from which the present liner is made which permits exact location of electrodes on a repeated basis on an individual's skins together with the tacking up of the liner upon the skin no matter what the individual's position or activity level that permits the liner to be readily applicable to bionics or robotics.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

What is claimed:

1. Method for making an improved liner and socket for an amputee who has a residual limb characterized as having a stump, a volume and shape and possible scar, skin graft, boney prominence, uneven limb volume, neuroma, pain, edema or soft tissue configurations, the method comprising:

a) constructing a first negative mold of the residual limb;

b) constructing a positive model of the residual limb from the residual limb negative mold;

c) reducing and building up the positive model for relief of certain tissue configurations;

d) placing a filler medium over the reduced positive model;

e) constructing a second negative mold of the reduced positive model with the filler medium thereon;

f) removing the filler medium; introducing a viscoelastic, energy absorbing, flexible polymer liner between the reduced positive model and the second negative mold;

g) removing the second negative mold from the liner;

h) constructing a third negative mold of the socket;

i) constructing a positive model of the socket;

j) reducing and building up the positive model of the socket to create weight bearing, compression and relief areas on the liner; and k) constructing the socket over the reduced and built up positive model of the socket.

* * * * *